United States Patent [19]

van Duyn

[11] Patent Number: Plant 6,610

[45] Date of Patent: Feb. 14, 1989

[54] ALSTROEMERIA NAMED WESTLAND

[75] Inventor: Cornelis van Duyn, NA Rijnsburg, Netherlands

[73] Assignee: Groot Associates II, Irvine, Calif.

[21] Appl. No.: 57,237

[22] Filed: Jun. 1, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Jackson & Jones

[57] ABSTRACT

A new Alstroemeria variety characterized by the brightly colored blossoms, the petals of which are bright purple with a yellow striped heart. The plant is early in flowering.

1 Drawing Sheet

BACKGROUND OF THE NEW PLANT

This new alstroemeria originated as a seedling selected from individual members of breeding stock maintained at Rijnsburg, Holland. The particular seedling was selected by me for propagation and testing because of its blossoms produced on upright stems. Specifically, the inner petals are deep purplish pink with vivid yellow striped hearts on white background (central). The outer petals are solid in deep purplish pink coloring. The inner petals have well defined longitudinal streaks or flecks of deep purplish red while the outer petals are limited to a solid purplish pink coloring. The selected plant was propagated by me at Rijnsburg, Holland through several generations of root divisions to establish that its distinctive characteristics hold true from generation to generation and appear to be firmly fixed.

Breeding efforts commenced in 1977 and propagation is currently being carried out at Rijnsburg, Holland. I discovered the new hybrid in 1981 at Rijnsburg. The nearest variety is the Alstroemeria called Evening Glow and my new variety, Westland, differs from the Evening Glow in that (1) the flowers are larger in size, (2) the petals have fewer stripes, (3) the flower stems are shorter and (4) the leaf color is lighter green.

DESCRIPTION OF THE DRAWING

This new variety of the Alstroemeria plant is illustrated by the accompanying photograph which shows a blooming umbel of the plant with buds and flowers in various stages of opening.

DESCRIPTION OF THE NEW PLANT

The following is a detailed description of my new Alstroemeria plant with color designations according to The National Bureau of Standards, Standard Reference Material, #2107, comprising the ISCC-NBS Centroid Color Charts and NBS Special Publication, #440.

THE PLANT

Origin: Seedling.
Parentage: Seed parent.
Classification: Alstroemeria hybrid.
Form: A generally erect bush having an upright stalk with flower-bearing branches in simple umbel arrangement at its top.
Height: About 1.45 meters.
Growth: Upright and strong.

Root stock: Tuberous.
Foliage:
- *Quantity.*—Normal.
- *Number of leaves.*—About 12–15 per stem.
- *Size of leaf.*—About 13×5 cm.
- *Shape of leaf.*—Parallel venation.
- *Texture.*—Smooth.
- *Color.*—Upper Side: Green. Under Side: Green.

THE BUD

Form: Long, round.
Size: Large.
- *Diameter.*—About 1.3 cm.
- *Length.*—About 4.0 cm.

Peduncle:
- *Length.*—About 15 cm.
- *Texture.*—Smooth.
- *Form.*—Erect.

THE FLOWER

Blooming habit: Profusely during early season in Spring.
Flower size: Medium.
- *Diameter.*—About 7 cm.
- *Depth.*—About 5 cm.

Borne: Terminal clusters.
Shape: Generally cup shaped with petal tips curling outwardly.
Petalage:
- *Number of petals.*—Six.
- *Arrangement.*—Two concentric circles of three.
- *Form.*—Broad ovate.
- *Texture.*—Soft.
- *Appearance.*—Velvety.

Color:
- *Outer petals.*—Deep purplish pink (No. 248).
- *Inner petals.*—Deep purplish pink (No. 248) with white (No. 263) center and vivid yellow (No. 82) heart. The inner petals have numerous generally longitudinal stripes or flecks of deep purplish red (No. 256).

Persistence: The flowers hang on and dry.
Main stem or stalk:
- *Length.*—About 15 cm.
- *Color.*—Green.
- *Character.*—Strong and upright.

Lasting quality of flower: About 3 weeks. As a cut flower, about 14 days.

REPRODUCTIVE ORGANS

Stamens:

*Number.*—Six.

*Arrangement.*—One opposite each petal.

Anthers:

*Size.*—About 0.8 cm×0.2 cm.

*Color.*—Greyish reddish purple (No. 245).

Filaments:

*Length.*—About 3.5 cm.

*Color.*—Light purplish pink (No. 249).

*Pollen.*—Grey.

Pistils:

*Number.*—One.

*Styles.*—Length: About 2–3 cm. Color: Light purplish pink (No. 249).

Fruit:

*Shape.*—Round.

*Color.*—Light brown.

This plant is particularly noted for the distinctive coloration of its flowers, which coloration does not clearly resemble that of any other Alstroemeria plant previously known to me. Inner petals with deep purplish red flecks on a deep purplish pink background with yellow striped hearts in the central portion on a white background and outer petals with a deep purplish pink coloring make this plant an attractive addition to the Alstroemeria family.

I claim:

1. A new and distinctive Alstroemeria cultivar, substantially as herein shown and described, characterized by the distinctive coloration of its medium and profusely blooming flowers.

* * * * *

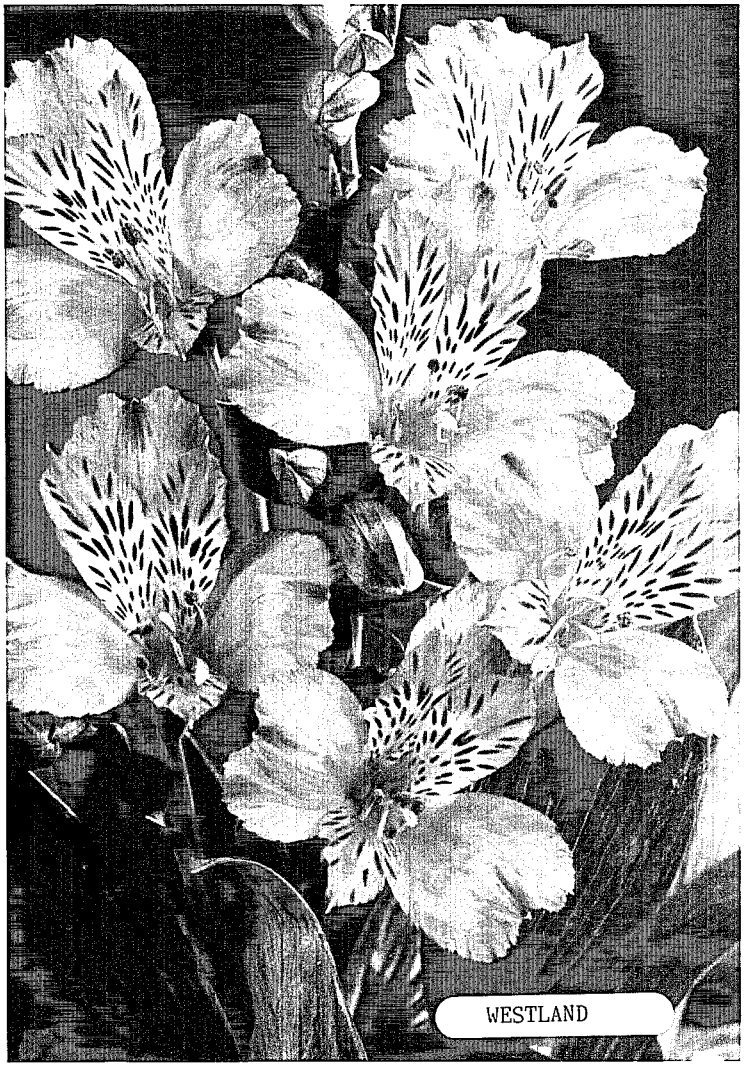
WESTLAND